US009511206B2

(12) United States Patent
Hofius et al.

(10) Patent No.: US 9,511,206 B2
(45) Date of Patent: Dec. 6, 2016

(54) ANCHORING NERVE BLOCK CATHETER

(71) Applicants: SRI INTERNATIONAL, Menlo Park, CA (US); THE BOARD OF TRUSTEES OF THE LELAND STANFORD JUNIOR UNIVERSITY, Palo Alto, CA (US); Chunyuan Qiu, Menlo Park, CA (US)

(72) Inventors: Jonathan Hofius, Menlo Park, CA (US); Manish Kothari, Menlo Park, CA (US); Chunyuan Qiu, Menlo Park, CA (US); Pablo E. Garcia, Menlo Park, CA (US); Karen S. Koenig, Menlo Park, CA (US)

(73) Assignee: SRI INTERNATIONAL, Menlo Park, CA (US)

( * ) Notice: Subject to any disclaimer, the term of this patent is extended or adjusted under 35 U.S.C. 154(b) by 0 days.

(21) Appl. No.: 14/791,460

(22) Filed: Jul. 5, 2015

(65) Prior Publication Data
US 2015/0306350 A1    Oct. 29, 2015

Related U.S. Application Data

(63) Continuation of application No. PCT/US2014/012128, filed on Jan. 17, 2014.
(Continued)

(51) Int. Cl.
*A61M 25/02* (2006.01)
*A61N 1/05* (2006.01)
(Continued)

(52) U.S. Cl.
CPC ........... *A61M 25/02* (2013.01); *A61M 25/005* (2013.01); *A61M 25/0053* (2013.01);
(Continued)

(58) Field of Classification Search
CPC .............. A61M 25/01; A61M 25/0138; A61M 25/0144; A61M 25/02; A61M 25/0026; A61M 25/0175; A61M 25/0059; A61M 19/00; A61M 25/012; A61M 25/0108; A61M 25/04; A61M 25/0074; A61M 25/0044; A61M 2025/0024; A61M 29/00; A61M 29/003; A61N 1/0551; A61B 18/1492
(Continued)

(56) References Cited

U.S. PATENT DOCUMENTS 4,419,819 A * 12/1983 Dickhudt ............... A61N 1/057
                                                                29/857
4,627,838 A * 12/1986 Cross ..................... A61M 25/04
                                                                604/105

(Continued)

FOREIGN PATENT DOCUMENTS

WO    WO 2012-159000    11/2012

*Primary Examiner* — Imani Hayman
*Assistant Examiner* — James D Ponton
(74) *Attorney, Agent, or Firm* — Richard Aron Osman (57) ABSTRACT

The invention relates to medical devices and, particularly, catheter medical devices. In an aspect is a nerve block catheter system comprising a dual-sheath catheter comprising an inner sheath and an outer sheath, wherein distal ends of the sheaths are connected, the inner sheath defines a fluid delivery lumen, and the outer sheath comprises a tissue lock movable between a collapsed position and an extended position, wherein the tissue lock forms a reversible tissue anchor when in the extended position, and an actuator connected to the proximate end of the catheter and configured to activate the tissue lock by sliding the outer sheath length-wise relative to the inner sheath.

20 Claims, 5 Drawing Sheets

Related U.S. Application Data (60) Provisional application No. 61/754,484, filed on Jan. 18, 2013, provisional application No. 61/845,238, filed on Jul. 11, 2013, provisional application No. 61/845,244, filed on Jul. 11, 2013, provisional application No. 61/845,248, filed on Jul. 11, 2013.

(51) Int. Cl.
*A61M 25/00* (2006.01)
*A61M 19/00* (2006.01)

(52) U.S. Cl.
CPC ............ *A61N 1/0551* (2013.01); *A61M 19/00* (2013.01); *A61M 25/0026* (2013.01); *A61M 2025/0056* (2013.01); *A61M 2025/0293* (2013.01); *A61M 2202/048* (2013.01)

(58) Field of Classification Search
USPC ............ 607/46, 116–154; 606/32, 33
See application file for complete search history.

(56) References Cited

U.S. PATENT DOCUMENTS

| | | | | |
|---|---|---|---|---|
| 4,983,165 A * | 1/1991 | Loiterman | ............ | A61M 25/01 604/95.03 |
| 5,290,249 A * | 3/1994 | Foster | ............ | A61B 17/34 604/174 |
| 5,305,740 A * | 4/1994 | Kolobow | ............ | A61M 16/04 128/207.14 |
| 5,443,449 A * | 8/1995 | Buelna | ............ | A61M 25/04 604/105 |
| 5,964,694 A * | 10/1999 | Siess | ............ | A61M 1/101 415/900 |
| 6,179,860 B1 * | 1/2001 | Fulton, III | ............ | A61M 25/04 606/116 |
| 2001/0012538 A1 * | 8/2001 | Ung-Chhun | ............ | A61L 27/34 427/2.25 |
| 2001/0056273 A1 * | 12/2001 | Ewers | ............ | A61M 25/10 604/509 |
| 2003/0195490 A1 * | 10/2003 | Boatman | ............ | A61L 29/06 604/525 |
| 2004/0049231 A1 | 3/2004 | Hafer | | |
| 2005/0288730 A1 * | 12/2005 | Deem | ............ | A61B 18/1492 607/42 |
| 2006/0184226 A1 | 8/2006 | Austin | | |
| 2008/0058757 A1 | 3/2008 | Pajunk et al. | | |
| 2008/0077172 A1 * | 3/2008 | Miller | ............ | A61B 17/3478 606/191 |
| 2009/0012541 A1 * | 1/2009 | Dahl | ............ | A61B 17/0401 606/151 |
| 2010/0145265 A1 * | 6/2010 | Min | ............ | A61M 25/0068 604/95.03 |
| 2011/0218529 A1 | 9/2011 | Garcia et al. | | |
| 2012/0059308 A1 * | 3/2012 | Hsu | ............ | A61M 19/00 604/21 |
| 2012/0136385 A1 * | 5/2012 | Cully | ............ | A61F 2/07 606/194 |

* cited by examiner

ANCHORING NERVE BLOCK CATHETER

CROSS-REFERENCE TO RELATED APPLICATIONS

This application claims priority to US Application Ser. Nos. 61/754,484, filed Jan. 18, 2013, 61/845,238, filed Jul. 11, 2013, 61/845,244, filed Jul. 11, 2013, and 61/845,248, filed Jul. 11, 2013, the disclosures of which applications are incorporated herein in their entireties.

This invention was made with government support under DHHS/Food and Drug Administration grant no. 1P50FD003782. The government has certain rights in the invention.

BACKGROUND

Increasing evidence from animal models to clinical studies have demonstrated the neurotoxicity of all inhalation anesthetic agents, which can produce apoptosis, prevent synaptogenesis, enhance neuro-inflammatory process and disturb Tau and aB1 production that link to Alzheimer's disease. The detrimental effect is especially troublesome in brain tissue of the young and elderly, which may further magnify and complicate their clinical primary pathology and jeopardize their long-term mental and physical wellbeing. Unfortunately, there is no known inhalation agent that is neuro-safe, and there are no known methods that can prevent detrimental effects from occurring if general anesthesia is indicated for a diagnostic or surgical procedure. Furthermore, the neurotoxicity of inhalation agents are dose dependent, which depend on the concentration as well as the duration of the exposure.

In light of the above new knowledge and the well-known safety and effectiveness profile of all regional anesthesia procedures, regional anesthesia is becoming more common alone or in combination with general anesthesia because it can effectively avoid or reduce the exposure of inhalation agents. The traditional dogma that general anesthesia is indicated for all who want it for their procedure is now under question, and more and more surgeons and using physicians have started to recommend their patients to consider regional anesthesia as part of their surgical care.

Regional anesthesia includes a wide variety of techniques that can be classified into two broad categories: central neuraxial nerve block and peripheral nerve bock. Spinal and epidural anesthesia are the two most common forms of central neuraxial nerve block. Peripheral nerve block includes a wide variety of procedures that target sensory or motor nerves peripheral to the spine canal. Nerve block is a fast growing area of anesthesia due to the improvement and quick adoption of ultrasound technology. However, inadvertent vascular puncture and unrecognized intravascular catheter migration are not uncommon, which may lead to local anesthetic toxicity and cause generalized seizure and cardiac arrest as well as failed nerve block.

The recent improvements in ultrasound guided nerve block, both central and peripheral, have popularized the procedure, but have failed to change the traditional clinical practice. Clinicians are still facing the same dilemma: The choice of single shot versus continuous nerve block, and receiving the same outcome: either too short or too long of duration of nerve block. A single shot nerve block can last as short as 4 hours or as long as 24 hours depending on the location of nerve block, medication used, and patient characteristics. Continuous nerve block is inherently difficult to perform, expensive, and outcomes are unpredictable due to catheter migration. As a result, nerve block is used purely as a pain management procedure during surgery or recovery, which is often at odds with functional recovery of a surgical patient. For example, prolonged femoral nerve block in total knee replacement (TKR) surgery can increase the risk of fall, delay rehabilitation, and prolong the length of hospital stay (LHS). On the other hand, ineffective femoral nerve block in TKR can also delay the rehabilitation, prolong the LHS, decrease patient satisfaction, and increase hospital cost.

Relevant art: US 20110218529; US 20070270928; and US 20010025169.

SUMMARY

In an aspect is an anchoring nerve block catheter system comprising: (A) a dual-sheath catheter comprising an inner sheath and an outer sheath, wherein the catheter and sheaths have proximate and distal ends, wherein distal ends of the sheaths are connected, the inner sheath defines a fluid delivery lumen, and the outer sheath comprises a tissue lock movable between a collapsed position and an extended position, wherein the tissue lock forms a reversible tissue anchor when in the extended position, and (B) an actuator connected to the proximate end of the catheter and configured to activate the tissue lock by sliding the outer sheath length-wise relative to the inner sheath, wherein the anchoring nerve block catheter system comprises a further improvement selected from: (i) the catheter is configured, when deployed in tissue with the tissue anchor activated, to apply a radial force to the tissue and therefore resist axial movement from an axial force of at least 200 g; (ii) a coil configured to: (a) provide echogenicity, wherein the coil is embedded in the inner sheath; (b) provide a bidirectional antenna configured to deliver electrical energy to a nerve and to transmit internal electricity from nerve electrical activities; or (c) improve anti-kinking of the catheter in locations prone to kinking, wherein the coil has varied wraps per inch length-wise or varied thickness along the length of the coil; (iii) the durometer or thickness of a wall of the catheter is varied to improve anti-kinking; (iv) (a) a coating on the tissue lock of a tissue ingrowth inhibitor substance sufficient to inhibit tissue ingrowth; (b) an anti-bacterial coating on the tissue lock; or (c) a covering over the tissue lock configured to inhibit tissue ingrowth and prevent backflow of anesthetic past the tissue lock between the tissue and the outer diameter of the outer sheath; (v) the inner sheath is configured to reduce or block fluid from leaking through the tissue lock when in the extended position, or wherein the inner sheath comprises one or more exit ports at the location of the tissue lock to allow multiple exit points for fluid; (vi) one or more protrusions at a skin entry point along the outer sheath configured to prevent backflow leakage of anesthetic; (vii) the tissue lock comprises living hinges strengthening the tissue lock when in the extended position; (viii) a weak point in the tissue lock promoting collapse of the tissue lock above an axial force or upon accidental removal of the catheter without deactivating the tissue lock; (ix) the actuator is a squeeze-type bi-stable mechanism configured such that when squeezed after implantation, it deactivates, thus preventing removal without deactivation; or wherein the catheter further comprises a deactivation mechanism that is separate from the actuator; (x) a lip or edge on the distal end of the catheter that forms over a lip or edge of a needle inserted through the inner sheath and is operative to avoid deploying the anchor during insertion; (xi) a fiberoptic camera or lens positioned through the catheter and configured to directly visualize a nerve or bolus post-block to ensure correct placement, or configured to detect the nerve; (xii) an echogenic treatment on the catheter distal end or tissue lock configured to improve echogenicity of the distal end or tissue lock.

In embodiments:

the catheter is configured, when deployed in tissue (or around nerve tissue) with the tissue anchor activated, to apply a radial force to the tissue and therefore resist axial movement from an axial force of at least 200 g;

the catheter system further comprises a coil configured to: (a) provide echogenicity, wherein the coil is embedded in the inner sheath; (b) provide a bidirectional antenna configured to deliver electrical energy to a nerve and to transmit internal electricity from nerve electrical activities; or (c) improve anti-kinking of the catheter in locations prone to kinking, wherein the coil has varied wraps per inch length-wise or varied thickness along the length of the coil;

the durometer or thickness of a wall of the catheter is varied to improve anti-kinking;

(a) a coating on the tissue lock of a tissue ingrowth inhibitor substance sufficient to inhibit tissue ingrowth; (b) an anti-bacterial coating on the tissue lock; or (c) a covering over the tissue lock configured to inhibit tissue ingrowth and prevent backflow of anesthetic past the tissue lock between the tissue and the outer diameter of the outer sheath;

the inner sheath is configured to reduce or block fluid from leaking through the tissue lock when in the extended position, or wherein the inner sheath comprises one or more exit ports at the location of the tissue lock to allow multiple exit points for fluid;

the catheter system further comprises one or more protrusions at a skin entry point along the outer sheath configured to prevent backflow leakage of anesthetic;

the tissue lock comprises living hinges strengthening the tissue lock when in the extended position;

the catheter system further comprises a weak point in the tissue lock promoting collapse of the tissue lock above an axial force or upon accidental removal of the catheter without deactivating the tissue lock;

the actuator is a squeeze-type bi-stable mechanism configured such that when squeezed after implantation, it deactivates, thus preventing removal without deactivation; or wherein the catheter system further comprises a deactivation mechanism that is separate from the actuator;

the catheter system further comprises a lip or edge on the distal end of the catheter that forms over a lip or edge of a needle inserted through the inner sheath and is operative to avoid deploying the anchor during insertion;

a fiberoptic camera or lens positioned through the catheter configured to directly visualize a nerve or bolus post-block to ensure correct placement, or configured to detect the nerve;

an echogenic treatment on the catheter distal end or tissue lock configured to improve echogenicity of the distal end or tissue lock; and the tissue lock comprises: (a) a plurality of parallel, length-wise slits defining a plurality of malecot extensions; or (b) a compliant material that bulges outward when axially compressed.

A method of using the nerve block catheter system as above, the method comprising one or more steps selected from: (1) navigating the nerve block catheter system so that the distal tip of the catheter is within pharmacological proximity to a nerve; (2) engaging the tissue lock; (3) delivering a medicament; (4) removing the needle; (5) repeatedly delivering a medicament, either in bolus or continuously, at physician discretion, to effect continuous pain management treatment; (6) disengaging the tissue lock; and (7) removing the catheter.

In embodiments:

step (1) is carried out with or without the use of nerve stimulation;

step (1) is carried out with or without the use of ultrasound guidance;

step (3) further involves detecting a resultant therapeutic effect after delivering the medicament;

the delivering of step (3) initiates a nerve block, and the method further comprises, if the nerve block fails to be initiated, or has worn off, detecting a resultant therapeutic effect.

In an aspect is a method of using nerve block catheter system as above, providing improved flow of care by enabling an using physician to perform the implantation procedure pre-operatively (as well as allowing the implantation to be performed intro-operatively or post-operatively).

In an aspect is a method of using nerve block catheter system as above, wherein the distance of catheter distal end to nerve is constrained to less than 1 mm, wherein there may be intermittent, temporary movements of the catheter distal end away from the nerve, but will return to within that range.

In an aspect is a nerve block catheter or catheter system substantially as disclosed herein and configured to support an axial force of 0-1000 g, preferably 0-750 g, more preferably 0-400 g.

In an aspect is a nerve block catheter or catheter system substantially as disclosed herein, comprising a coil and configured to: (a) create echogenic catheter by embedding coil in inner sheath; (b) add small deformities/divots/pits/air pockets to the coil to increase echogenicity; (c) use the coil as a bidirectional antenna; and/or (d) vary the wraps/inch along length to improve antikinking in locations prone to kinking (proximally), for example, i. wherein the section proximal to the skin has 50 wraps/inch (WPI) coil, and the section embedded under the skin has 100 WPI coil, wherein the thickness of the coil can also be varied, e.g. to decrease coil thickness, decrease flexibility, etc.; and/or ii. wherein the durometer and/or wall thickness of the catheter lumen are varied to vary the flexibility to account for different flexibility requirements between the sections proximal vs. distal to the skin.

In an aspect is a nerve block catheter or catheter system substantially as disclosed herein, comprising a coil and configured to prevent tissue ingrowth by: (a) coating the tissue lock with substance like hyalase to inhibit tissue ingrowth; (b) covering with silicone cover, balloon, extra sheath, to inhibit ingrowth, and/or also prevent backflow of anesthesia/analgesia past the tissue lock in between the tissue and outer diameter of the outer sheath.

In an aspect is a nerve block catheter or catheter system substantially as disclosed herein, comprising an inner sheath configured to reduce or block anesthesia/analgesia from leaking through the tissue lock, and/or comprising one or more exit ports on the inner sheath at the location of the tissue lock to allow multiple exit points for the anesthesia/analgesia.

In an aspect is a nerve block catheter or catheter system substantially as disclosed herein, comprising one or more protrusions at skin entry point configured to prevent backflow leakage.

In an aspect is a nerve block catheter or catheter system substantially as disclosed herein, comprising living hinges at each end of the malecot extensions and in the middle operative to strengthen malecot extension.

In an aspect is a nerve block catheter or catheter system substantially as disclosed herein, comprising one or more fail safe modes comprising: (a) a weak point/notch/thinner section in the tissue lock to promote the collapse of the tissue lock above an axial force (supra) so that it collapse upon accidental removal of the catheter without deactivating; (b) a bi-stable mechanism for squeezing to activate/deactivate so that when you squeeze it after implantation, it will always deactivate, thus preventing removal without deactivation; (c) the mechanism only used for deactivation so the using physician can still use a slider/button, etc. to activate.

In an aspect is a nerve block catheter or catheter system substantially as disclosed herein, wherein the tip of the catheter comprises a lip or edge that forms over a lip/edge of the needle and operative to avoid deploying the anchor during insertion.

In an aspect is a nerve block catheter or catheter system substantially as disclosed herein, and comprising a thin, fiberoptic camera or lens that goes through the catheter (through the fluid delivery lumen, a second lumen, or embedded in the wall) to directly visualize the nerve post-block to ensure correct placement, and which optionally can be used during initial implantation or for follow-up blocks, and provide, e.g. comparison to initial snapshot to ascertain whether it is still in the same location, and/or wherein an infrared camera or other wavelength camera is used to detect the nerve.

In an aspect is a nerve block catheter or catheter system substantially as disclosed herein, comprising improved echogenicity and breakage recovery, e.g. by coating the catheter tip and/or tissue lock with an echogenic treatment such as ECHO-COAT™ (i.e., a surface treatment which traps microscopic air bubbles, creating highly efficient ultrasonic reflectors) to improve echogenicity of the tip and/or tissue lock, and optionally also make finding those parts easier to find in the case where any part breaks off in the tissue. As used herein, the term "echogenic treatment" includes echogenic coatings that provide either hypoecho or hyperecho enhancement.

In an aspect is a method of using nerve block catheter or catheter system substantially as disclosed herein, comprising steps: tracking the nerve with the electrode; placing the catheter; engaging the lock; delivering a medicament; detecting a resultant therapeutic effect; disengaging the lock; and/or removing the catheter.

In an aspect is a method of using nerve block catheter or catheter system substantially as disclosed herein, providing improved flow of care by enabling the using physician to perform the implantation procedure pre-operatively vs. intra-operatively.

In an aspect is a method of using nerve block catheter or catheter system substantially as disclosed herein, wherein the distance of catheter tip to nerve is constrained to 1 mm, or 0.5 mm, wherein there may be intermittent, temporary movements away from the nerve, but will return to within that range (safety is key, should allow macro movement and anchor remains anchored to same local tissue, so when that local tissue returns to its nominal location, so will the catheter tip).

In an aspect is a method of making a nerve block catheter or catheter system substantially as disclosed herein, comprising assembling the catheter or system from one or more components.

In an aspect is an anchoring nerve block catheter system comprising: (A) a dual-sheath catheter comprising an inner sheath and an outer sheath, wherein the catheter and sheaths have proximate and distal ends, wherein distal ends of the sheaths are connected, the inner sheath defines a fluid delivery lumen, and the outer sheath comprises a tissue lock movable between a collapsed position and an extended position, wherein the tissue lock forms a reversible tissue anchor when in the extended position, and (B) an actuator connected to the proximate end of the catheter and configured to activate the tissue lock by sliding the outer sheath length-wise relative to the inner sheath. When the catheter is inserted extravascularly in a patient, the tissue lock is configured to anchor the catheter distal end to surrounding tissue such that the catheter distal end is in an initial position adjacent to, and a predetermined distance from, a target nerve, but away from a blood vessel, and the catheter distal end returns to the initial position even after a displacement. Furthermore the tissue lock is configured to collapse under a predetermined applied axial force. Furthermore, the catheter is configured to accept a needle positioned therein, wherein a distal end of the needle is at a fixed distance from the distal end of the catheter, and wherein the catheter system is configured to maintain the fixed distance between the distal ends of the needle and catheter during implantation of the needle/catheter in a patient, and wherein the catheter system is configured to maintain the fixed distance between the distal ends of the needle and catheter during deployment of the tissue lock.

Any of the catheter systems described herein may further be combined with a needle disposed within the inner sheath. Therefore, in an aspect is a kit comprising the catheter system described herein in combination with a needle disposed within the inner sheath.

These and other aspects will be apparent to those of skill in the art based on the disclosure provided herein.

DETAILED DESCRIPTION OF PARTICULARLY EMBODIMENTS

The technical field of the invention relates to medical devices and, particularly, catheter medical devices.

In an aspect is an anchoring nerve block catheter system comprising: (A) a dual-sheath catheter comprising an inner sheath and an outer sheath, wherein the catheter and sheaths have proximate and distal ends, wherein distal ends of the sheaths are connected, the inner sheath defines a fluid delivery lumen, and the outer sheath comprises a tissue lock movable between a collapsed position and an extended position, wherein the tissue lock forms a reversible tissue anchor when in the extended position, and (B) an actuator connected to the proximal end of the catheter and configured to activate the tissue lock by sliding the outer sheath length-wise relative to the inner sheath.

Figure 9:
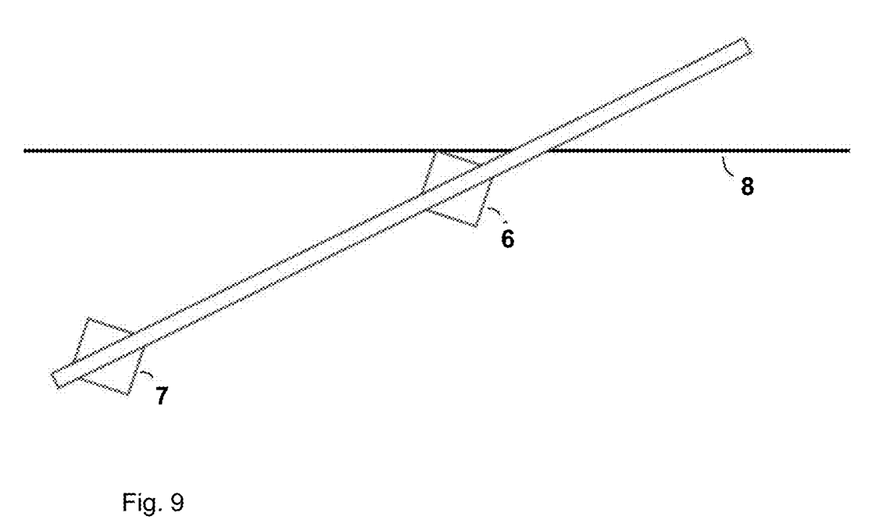
FIG. 9 is a drawing of a catheter according to an embodiment comprising a protrusion at a skin entry point along the outer sheath configured to prevent backflow leakage of anesthetic.

The anchoring nerve block catheter system comprises a further improvement selected from the following 12: (i) the catheter is configured, when deployed in tissue with the tissue anchor activated, to apply a radial force to the tissue to resist axial movement from an axial force of at least 200 g; (ii) a coil configured to: (a) provide echogenicity, wherein the coil is embedded in the inner sheath; (b) provide a bidirectional antenna configured to deliver electrical energy to a nerve and to transmit internal electricity from nerve electrical activities; or (c) improve anti-kinking of the catheter in locations prone to kinking, wherein the coil has varied wraps per inch length-wise or varied thickness along the length of the coil; (iii) the durometer or thickness of a wall of the catheter is varied to improve anti-kinking; (iv) (a) a coating on the tissue lock of a tissue ingrowth inhibitor substance sufficient to inhibit tissue ingrowth; (b) an anti-bacterial coating on the tissue lock; or (c) a covering over the tissue lock configured to inhibit tissue ingrowth and prevent backflow of anesthetic past the tissue lock between the tissue and the outer diameter of the outer sheath; (v) the inner sheath is configured to reduce or block fluid from leaking through the tissue lock when in the extended position, or wherein the inner sheath comprises one or more exit ports at the location of the tissue lock to allow multiple exit points for fluid; (vi) as shown in FIG. 9, one or more protrusions 6 separate from the tissue lock 7 and at a skin entry point 8 along the outer sheath configured to prevent backflow leakage of anesthetic; (vii) the tissue lock comprises living hinges strengthening the tissue lock when in the extended position; (viii) a weak point in the tissue lock promoting collapse of the tissue lock above an axial force or upon accidental removal of the catheter without deactivating the tissue lock; (ix) the actuator is a squeeze-type bi-stable mechanism configured such that when squeezed after implantation, it deactivates, thus preventing removal without deactivation; or wherein the catheter further comprises a deactivation mechanism that is separate from the actuator; (x) a lip or edge on the distal end of the catheter that forms over a lip or edge of a needle inserted through the inner sheath and is operative to avoid deploying the anchor during insertion; (xi) a fiberoptic camera or lens positioned through the catheter configured to directly visualize a nerve or bolus post-block to ensure correct placement, or configured to detect the nerve; and (xii) an echogenic treatment on the catheter distal end or tissue lock configured to improve echogenicity of the distal end or tissue lock. The anchoring nerve block catheter system may comprises more than one such improvement, such as 2, 3, 4, 5, 6, 7, 8, 9, 10, or 11 of the improvements in any combination (and all possible combinations are intended to be within the scope of the invention). The anchoring nerve block catheter system may comprise all 12 of the improvements. Further details of these improvements and other aspects of the catheter systems are provided below. As used herein, the term "nerve block" is intended to include both central neuraxial nerve block and peripheral nerve block.

System Components—Catheter

The catheter comprises an inner sheath and a conformal outer sheath. (As used herein, the term "catheter" refers to the portion of the device comprising the inner and outer sheath, whereas the term "catheter system" refers to the catheter portion as well as the actuator portion.) The catheter, inner sheath, and outer sheath have proximal and distal ends, and the proximal ends of the inner and outer sheaths are each connected to an actuator. Throughout this specification, the terms "distal end" and "tip" are used interchangeably.

The distal ends of the inner and outer sheaths are connected in a fixed relationship (i.e., they cannot move relative to one another). Between their proximal and distal ends, the inner and outer sheaths are not connected and therefore can move relative to one another. The outer sheath can slide relative to the inner sheath (i.e., the inner sheath is slidably disposed within the outer sheath), provide that their distal ends remain connected.

Figure 6:
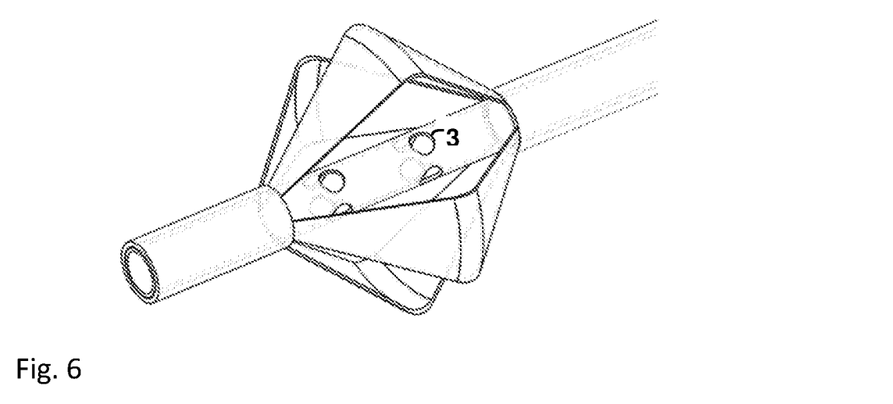
FIG. 6 is a drawing of a catheter according to an embodiment, including a malecot tissue lock, with multiple exit ports on the inner sheath.

The inner sheath defines a fluid delivery lumen. The inside diameter of the inner sheath defines the width of the fluid delivery lumen, which (in part) determines the volume of fluid that can be delivered via the catheter system. The inside diameter can be any appropriate value. Example inside diameters for the inner sheath are in the range 0.5-3.5, 0.5-3, or 0.5-2 mm, or less than 3.5, 3, 2.5, 2, or 1.5 mm, or greater than 0.5, 1, 1.5, 2, 2.5, or 3 mm. The inner sheath may be completely homogeneous, or may, in embodiments, comprise one or more exit ports in the form of holes. For example, as shown in FIG. 6, the inner sheath comprises one or more exit ports 3, at the location of the tissue lock to allow one or multiple exit points for fluid traveling through the fluid delivery lumen. For example, the inner sheath comprises 2-30, 2-15, or 2-5 rows of exit ports, or greater than 2, 5, 10, or 15 rows, or less than 30, 20, or 15 rows, with each row comprising 2-50, 2-30, or 2-15 ports, or greater than 2, 5, 10, or 20 ports, or less than 50, 30, or 20 ports. The rows can be arranged symmetrically around the circumference of the inner sheath in order to dispense provided fluid equally in all directions, or the rows can be arranged non-symmetrically in order to dispense fluid in an asymmetric pattern.

When inserted in a patient, the outer sheath directly contacts the patient's tissue, while the inner sheath does not come into direct contact with the patient's tissue (with the exception of the cross section of the tip of the inner sheath). Furthermore, when inserted in a patient, at least a portion of the outer sheath is directly visible to the physician using the system whereas the entire inner sheath remains hidden from view. The visible portion of the outer sheath is the length of the catheter that remains outside of the patient's body during use of the catheter.

In embodiments, the outer sheath comprises protrusion at a skin entry point (along the length of the outer sheath) to prevent backflow leakage (i.e., leakage of fluid out of the skin). For example, the system may comprise a ring that can be adjusted along the length of the outer sheath. The ring compresses the outer sheath and determines the location of the proximal protrusion to adjust for different penetration depths. The ring functions as a collar, an example being an o-ring, whose position could be adjust along the length of the outer sheath. The using physician can position the ring so that it is located at the skin entry point and can therefore block the leakage of fluid at the skin entry point.

The outer sheath comprises a tissue lock movable between a collapsed position and an extended position. The tissue lock is reversible—i.e., it can move from collapsed to extended position and return to the collapsed position an indefinite number of repetitions. The tissue lock provides anchoring of the catheter distal end such that the catheter can deliver a medicament to a controlled location within the patient.

Movement between collapsed and extended positions is caused by sliding the outer sheath relative to the inner sheath (while the distal ends of the inner and outer sheaths remain connected and fixed); such sliding is caused by activation of the actuator, which is connected directly to the outer sheath as described in more detail herein.

The tissue lock forms a reversible tissue anchor when in the extended position. The tissue anchor is the result of force exerted on surrounding tissue by the tissue lock. As described herein, the force can be adjusted to customize the operation of the catheter. Selection of the amount of force exerted by the tissue lock can be accomplished upon manufacture, such as by manufacturing the tissue lock with specific physical dimensions (e.g., creating a larger or smaller diameter of the tissue lock in the extended position) or with specific material properties (e.g., using a more or less stiff material, etc.).

Figure 4:
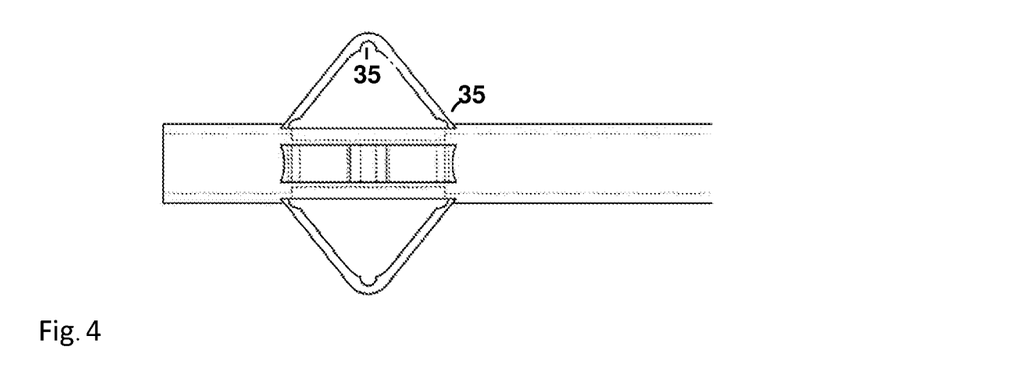
FIG. 4 is a drawing of a catheter according to an embodiment, including a malecot tissue lock, with living hinges at the ends and middle of each malecot protrusion

In embodiments, the tissue lock is a malecot and the outer sheath comprises a plurality of parallel length-wise slits defining a plurality of malecot extensions. The number of slits may vary and determines the number or malecot extensions—for example, four slits results in four malecot extensions. In embodiments the outer sheath comprises 2-20 slits, or 3-10 slits, or exactly 3, 4, 5, 6, 7, 8, 9, or 10 slits. Each malecot extension may comprise one or more living hinges or one or more mechanical hinges, or a combination thereof. Such hinges operate to increase the force exerted by the extensions on surrounding tissue. For example, such as shown in FIG. 4, living/mechanical hinges 35 can be located at the center line of each malecot extension and, optionally, at the proximal and/or distal ends of each extension (see also, e.g., FIG. 1). Where the tissue lock is a malecot, the force exerted by each malecot extension, the number of extensions, the location(s) of any living/mechanical hinges, the materials used, and other factors determine the amount of axial force that the catheter can resist, and also determine the amount of force that the malecot extensions exert on surrounding tissue when in the extended position.

In embodiments, the tissue lock is a bulging tissue lock, and the tissue lock comprises a compliant material that bulges outward when axially compressed. The compliant material may comprise a material compositionally different from other portions of the outer sheath, such as a material composition providing less stiffness. Alternatively, the compliant material may be the same compositionally as other parts of the outer sheath but may differ in mechanical properties—e.g., the compliant material may be thinner (e.g., equal to or more than 10, 20, 30, 40, or 50% thinner). Where the tissue lock is a bulging tissue lock, the force exerted by the bulged tissue lock on surrounding tissue when in the extended position is determined primarily by the stiffness of the compliant material and the size of the bulge (e.g., the change in diameter of the tissue lock when moved from the collapsed to the extended position). The bulging tissue lock may comprise one or more living or mechanical hinges as described above for malecot tissue locks.

In embodiments, the tissue lock comprises barbs or other protrusions that further anchor the catheter to adjacent tissue. The barbs may be disposed on a portion or on the entire surface of the tissue lock or the body of the catheter. The barbs may be configured to increase the amount of axial force that the catheter can resist, and further configured to be releasable (e.g., to fail) above a certain predetermined force such that the tissue lock of the catheter remains reversible. In an embodiment, the barbs are sufficiently small such that they do not significantly damage surrounding tissue when the tissue lock is engaged. The barbs may be either rigid or flexible, and may, in embodiments, be made from an absorbable material. Microbarbs can be as small as 0.25-1 mm, or 0.25-0.5 mm. In embodiments, microbarbs are difficult to see with the naked eye, and can provide anchoring when tissue collapses around them. Microbarbs may also be used in conjunction with the malecot anchor described herein.

In embodiments, the catheter can resist axial movement by an applied axial force of at least 200, 250, 300, 350, or 400 g when the tissue lock is in the extended position. Also in embodiments, the catheter can resist radial movement from an applied radial force when the tissue lock is in the extended position. By "resist axial movement" is meant that the catheter (particularly, the catheter tip) moves less than 2, 1.5, 1, or 0.5 mm relative to the surrounding tissue to which it is anchored. By "resist radial movement" is meant that the catheter (particularly, the catheter tip) rotates less than 20, 15, 10, 5, or 1 degree relative to the surrounding tissue to which it is anchored.

Figure 5:
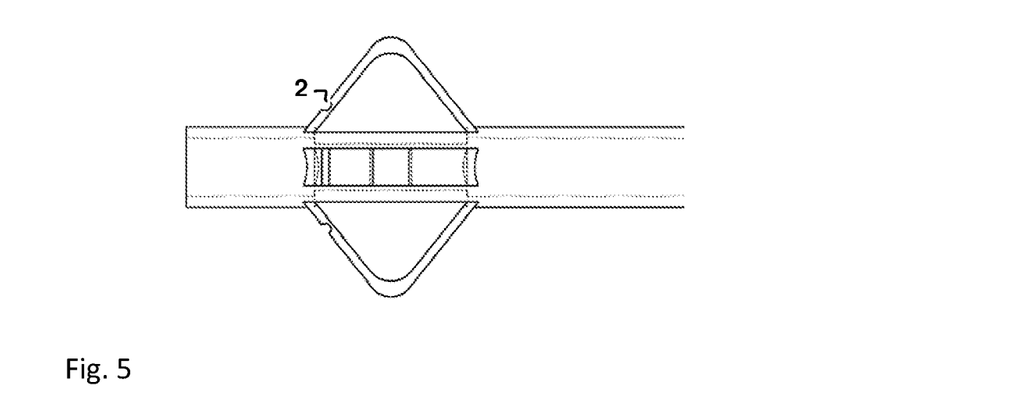
FIG. 5 is a drawing of a catheter according to an embodiment, including a malecot tissue lock, with a locking hinge.

In embodiments, such as shown in FIG. 5, the tissue lock comprises a weak point 2 (e.g., a notch or thinner section at the distal end of the tissue lock or at the midpoint along the length of the tissue lock) to promote the collapse of the tissue lock above a given axial force. For example, the tissue lock will collapse upon accidental removal of the catheter without deactivating the tissue lock. Because of such safety feature, the catheters described herein have an upper bound on the amount of axial force that can be resisted when the catheter is deployed in a patient. Such upper bound may be, for example, 1000, 900, 800, 700, 600, 500, 400, or 300 g. Similarly, the tissue lock may comprise a weak point to promote the collapse of the tissue lock above a given radial force. The tissue lock is configured to collapse under any of these axial forces such that forces exceeding these values will not cause damage to the surrounding tissue. Weak points include notches, holes, slits, etc. that are cut or otherwise placed into the tissue lock (malecot, bulge, etc.) at various locations along the tissue lock. Weak points could also be created by applying heat or energy to weaken the material in various locations.

It is desirable to avoid kinking of the catheter, and various points along the length of the catheter may require varying flexibility (particularly for portions of the catheter that remain outside of the patient compared with portions that enter the patient). Accordingly, the catheter systems described herein may include one or more improvements that reduce or eliminate kinking, and/or alter the flexibility of the catheter. Examples of such improvements include varying the durometer of the catheter and varying the thickness of the catheter walls. Generally, variation of the durometer or flexibility of the material will be most effective when applied to the inner sheath (as opposed to the outer sheath), particularly in embodiments where the inner sheath is stronger and/or thicker than the outer sheath.

For example, the durometer (i.e., hardness) of the catheter material(s) may be varied in order to provide varying flexibility and varying resistivity to kinking. Generally, a higher durometer indicates a material that is more prone to kinking. In an embodiment, the portion of the catheter intended to remain outside of the patient (e.g., the proximal portion of the length of the catheter) may be made with a lower durometer compared with the portion intended to enter and remain inside the patient (e.g., the distal portion of the length of the catheter). The durometer of polymeric materials can be varied throughout the length of the catheter during the extrusion process, e.g., by extruding with different durometer pellets, or by treating the polymer differently such as by exposure to UV to change the properties of the polymer. Example durometer measures are in the range of Shore20 A-Shore100 A.

Also for example, the thickness of the catheter may be varied in order to provide varying flexibility and varying resistivity to kinking. Reference to the "wall" of the catheter refers to the combined inner and outer sheaths—therefore the wall thickness is the combined thickness of the two sheaths. Generally, thinner walls are more prone to kinking. In embodiments, the thickness of the catheter wall in at the distal end of the catheter is in the range 0.01-0.075 inches, and the thickness of the catheter wall in at the proximal end of the catheter is in the range 0.025-0.10 inches. Within these values, the individual thicknesses of the outer and inner sheath walls can be any appropriate value to obtain the desired characteristics (stiffness, strength, etc.). In embodiments, the inner sheath wall will be thicker than the outer sheath wall, such as 5, 10, 25, 50, or 100% thicker. In embodiments the thicknesses of the inner and outer sheath walls are the same, and in other embodiments the thickness of the outer sheath wall is greater than that of the inner sheath wall (e.g., 5, 10, 25, 50, or 100% greater). The thickness between the proximal and distal ends may vary continuously and linearly, or may undergo a more rapid change near a skin-entry point (or an expected skin-entry point) of the length of the catheter.

In embodiments, the catheter comprises a depth gauge for indicating to the using physician the depth that the catheter has been inserted (e.g., below the patient's skin). For example, stripes or other marks may be present along the length of the catheter and disposed on the external side of the outer sheath, including at the tip and optionally on the tissue lock. The stripes/marks can be color coded or otherwise marked to indicate depth. In embodiments, such marks may also be used to ensure all parts of the catheter remain intact during implantation. The stripes/marks may indicate preferred depths, particularly where the catheter comprises sections that are more or less prone to kinking. For example, where the catheter comprises a section highly resistive to kinking, the depth gauge may indicate that such section is to remain outside of the patient.

In embodiments, the catheter comprises a lip or edge on the distal end of the catheter that forms over a lip or edge of a needle inserted through the inner sheath. For example, the lip/edge of the catheter forms a stop against which the needle can push as the catheter and needle combination is inserted into a patient. During insertion, the catheter encounters axial forces, which, via friction, can result in compression of the outer sheath and unintended extension of the tissue lock. The catheter lip may be part of the inner sheath, the other sheath, or both inner and outer sheaths. Thus, the catheter lip or edge is operative to avoid deploying the anchor during insertion. The lip prevents unintended compression of the catheter and particularly of the outer sheath, which would potentially result in unintended deployment of the anchor. See, for example, FIG. 3, described in more detail herein.

Figure 7:
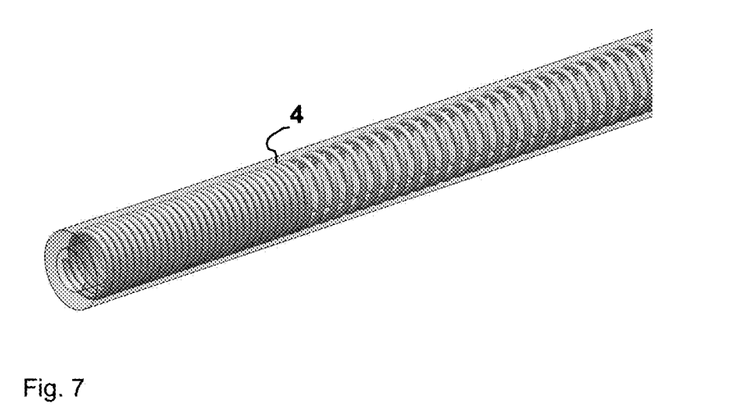
FIG. 7 is a drawing of a catheter according to an embodiment, including a coil, with variable wraps/inch for the coil.

In embodiments as shown in FIG. 7, the catheter comprises a coil 4. The coil may be configured to: (a) provide echogenicity; (b) provide a bidirectional antenna configured to deliver electrical energy to a nerve and to transmit internal electricity from nerve electrical activities; or (c) improve anti-kinking of the catheter in locations prone to kinking, wherein the coil has varied wraps per inch length-wise or varied thickness along the length of the coil.

In embodiments, the coil is configured to provide echogenicity. For example, the coil is embedded in the inner sheath and is prepared from an echogenic material. Suitable materials include metals such as stainless steel. In embodiments, small deformities and/or divots and/or pits are present in the coil to increase echogenicity thereof. Imparting echogenicity to the catheter via an echogenic coil enhances visualization of the location of the catheter tip. Such enhancement aids placement of the catheter and monitoring of the catheter after placement.

In embodiments, the coil is configured to provide a bidirectional antenna configured to deliver electrical energy to a nerve and to transmit internal electricity from nerve electrical activities. As such, the coil can deliver external electricity and therefore operates as a stimulating catheter. Furthermore, the coil can transmit internal electricity such as native or evoked nerve electrical activities. Such bidirectional transmission can be used, for example, to triangulate the location of the nerve block during navigation or nerve-seeking operations.

In embodiments, the coil is configured to improve anti-kinking of the catheter in locations prone to kinking. Anti-kinking measures for the inner and outer sheath are described herein, and improved anti-kinking can be obtained by using (in the alternative or in addition) a coil embedded, for example, in the inner sheath. Anti-kinking from such an embedded coil can be obtained in a variety of ways. For example, the coil may have wraps per inch (i.e., pitch) that vary length-wise along the length of the coil. Generally, fewer wraps per inch (i.e., a longer pitch) results in a more flexible/bendable coil, and therefore more resistance to kinking. Such a situation is particularly suitable for the proximal portion of the catheter, which is the part intended to remain outside of the patient. Conversely, the distal portion of the catheter benefits from a shorter pitch and therefore a coil that is less bendable, and less resistant to kinking. Alternatively or in addition, the coil may have varied thickness along the length of the coil. In this context, "thickness" refers to the diameter of the strand that forms the coil. Generally, greater thickness results in greater resistance to kinking. As with varied pitch, the thickness can be varied according to the location along the length of the catheter—e.g., greater thickness in external/proximal portions and lesser thickness in internal/distal portions. In embodiments, the section of the catheter that is closest to a skin entry point (which section may be indicated using depth gauges as described herein) may be configured for maximal anti-kinking, e.g., by having greatest thickness or longest pitch.

In embodiments, the coil may be configured for more than one of the above-mentioned functions. Furthermore, in embodiments, the coil may be prepared from a non-ferrous material (e.g., aluminum, zinc, titanium, etc.) to promote compatibility with MRI scanning.

One or more coatings may be present along the catheter. Such coatings may be suitable for enhancing echogenicity, tissue ingrowth inhibition, or antibacterial properties of the catheter.

In embodiments, the catheter comprises an echogenic treatment. An example echogenic treatment is ECHO-COAT®. An echogenic treatment may be applied to any portion of the catheter, such as the catheter distal end (i.e., tip), or to the tissue lock, or to the distal portion, or to the entire length of the catheter. The echogenic treatment may be used to improve echogenicity of the tip and/or tissue lock. The echogenic treatment may also be used to aid in finding any parts of the catheter that may break off inside the patient (e.g., within the patient's tissue). In embodiments, an echogenic treatment is used on the tip and/or tissue lock, wherein such coating is dissimilar to a echogenic treatment used for the rest of the catheter. The dissimilarity may be either in pattern or intensity, with the purpose of more easily identifying the tip or tissue lock. (e.g., diagnose or differential diagnosis of inadequate nerve block down stream).

In embodiments, the catheter comprises a coating that inhibits ingrowth of tissue (and/or fibrosis). An example ingrowth inhibitor coating is the compound hyalase. Further examples include glucocorticoids (steroids, known to inhibit fibroblast cells and inhibit scar formation), methotrexate (a chemotherapy that inhibits cell proliferation), MED-ERMA® (*allium cepa* extract gel, used to treat stretch mark or scar tissue), and the like. The ingrowth inhibitor is present to ensure that, over long implantation times (with "long" meaning at least 5 days, or greater than or equal to 5, 7, 9, 11, 14, 21, or 28 days), unwanted ingrowth of tissue on the tissue lock or other components of the catheter is minimized or prevented. Alternatively or in addition to an ingrowth inhibitor coating, an ingrowth inhibitor compound can be delivered through the lumen of the catheter while the catheter is implanted. The ingrowth inhibitor coating can be present over the entire catheter length, or over a select portion such as the tissue lock, the distal end, or the distal portion of the catheter.

In embodiments, the catheter comprises an antibacterial coating. Example antibacterial coatings include silver or copper particles, chitosan, or the like. Antibacterial coatings are particularly suitable for catheters intended for long implantation times as described herein. The antibacterial coating can be present over the entire catheter length, or over a select portion such as the tissue lock, the distal end, or the distal portion of the catheter.

Any combination of the echogenic, antibacterial, and ingrowth inhibitor coatings may be present. In embodiments, two or more such coatings are present, such as an antibacterial coating and an ingrowth inhibitor coating (such combination is particularly suitable for catheters intended for long implantation times). In embodiments, all three coatings are present. Furthermore, different sections of the catheter may be coated differently. For example, the distal end may be coated with an echogenic treatment while the tissue lock and distal portion of the catheter (including or not including the distal end) may be coated with an antibacterial coating. Other combinations and arrangements are possible and within the scope of the disclosure.

The catheters may be of any suitable length, and the intended application will typically influence the desired length. For example, the catheter length may be in the range 5-30 cm. In embodiments, the catheter is configured such that approximately 10-50% of the catheter length is intended to remain outside of the patient (and is referred to herein as the "proximal portion"), whereas approximately 50-90% of the catheter length is intended to be inserted into the patient (and is referred to herein as the "distal portion").

System Components—Catheter System

The catheter system comprises the catheter and an actuator. A variety of actuators are suitable. The actuator is a mechanism that is located at the proximal end of the catheter and directly connects to the proximal end of the outer sheath. The actuator operates in a first action to reversibly and axially slide the outer sheath relative to the inner sheath, thereby axially compressing the outer sheath. The axial compression causes the tissue lock to move from the collapsed position to the extended position. The actuator also operates in a section action (e.g., via the reverse of the first action) to decompress the outer sheath, thereby moving the tissue lock from the extended position to the collapsed position.

The actuator may further comprise a lock to ensure that the position of the outer sheath (and therefore the status of the tissue lock) does not creep or otherwise undesirably change.

In embodiments, the actuator is a bistable mechanism that is activated and deactivated by squeezing the hub. For example, the bi-stable mechanism is configured such that, any time the mechanism is squeezed after implantation, it will always deactivate the tissue lock (i.e., the default position is an extended tissue lock), thus preventing accidental removal without deactivation.

In embodiments, the actuator is a button that activates the tissue lock.

In embodiments, the actuator is a spring-loaded button activation. This configuration works with a spring concentric to the sheaths. The button releases and pulls back on the spring to push/pull on the outer sheath.

In embodiments, the actuator is a crank and wheel mechanism. Such mechanism converts a rolling motion to a linear motion of the sheath, therefore activating the anchor.

In embodiments, the actuator is a variation of the Scotch Yolk Mechanism. Such mechanism converts a rolling motion to a linear motion of the sheath, therefore activating the anchor In embodiments, the actuator is a twisting distal hub. The advantages of such embodiment are that the twisting motion is normal to the long axis of the catheter, therefore, the physician will not inadvertently advance or retract the catheter during activation.

In embodiments, the actuator is a roll wheel. The advantages of such embodiment is that it has a shorter overall length, and can be activated with one hand.

In embodiments, the actuator is a push/pull linear slider. The advantages of such embodiment are that it has a shorter overall length, can be activated with one hand, and has fewer moving parts than roll wheel.

In embodiments, the catheter system comprises a deactivation mechanism—i.e., a mechanism separate from the actuator and used only for deactivation. In such embodiments the physician can still use a slider/button/knob, etc. to activate.

In embodiments the actuator is part of a hub providing a suitable grip for the using physician. The hubs for the catheter may take any suitable shape, for example, round, square, triangular, or elliptical. Any such shape may further include ridges, protrusions, divots, dimples, variations in surface finish, variations in body dimensions, or the like in order to enhance grip.

Figure 8:
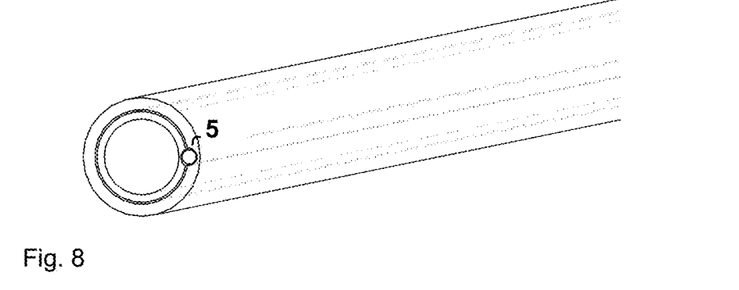
FIG. 8 is a drawing of a catheter according to an embodiment, including a camera between two sheaths.

In embodiments, the catheter system further comprises a fiberoptic camera or lens positioned through the catheter configured to directly visualize a nerve (and/or bolus) post-block to ensure correct placement, or configured to detect the nerve. In embodiments, the camera/lens is positioned through the fluid delivery lumen, or through a second lumen, or through the catheter wall. In embodiments as shown in FIG. 8, the camera/lens 5 is positioned between the inner and outer sheaths, or may be positioned within a lumen that is separate from and parallel to the fluid delivery lumen, or may be embedded within the inner or outer sheath. In embodiments, the system is configured to send to the using physician a direct image from the camera, or an algorithm is used that calculates proximity based on processing the images of the nerve/bolus from the camera. The proximity of the catheter can be relayed to the physician along with suggestions on ideal proximity (i.e. "not close enough", "too close", or "just right"). The camera/lens can be used during initial implantation of the catheter and/or for follow-up blocks. For a follow-up, comparison to initial images can be used to ascertain whether the catheter tip remains in the initial location, or the extent to which the catheter tip has moved. In embodiments, the camera/lens is used to aid in the correction of any displacement that occurs. In embodiments, an infrared camera or other wavelength camera can be used to detect the nerve.

In embodiments, the catheter system further comprises a needle lock configured to lock a needle into a set orientation so the needle tip bevel is set at a consistent and predictable angle during insertion.

In embodiments, the catheter system comprises an outer sheath collar. The outer sheath collar provides a means (e.g., a lip, edge, etc.) for the actuator to pull/push on the outer sheath. The outer sheath collar can be used with any actuator to assist in the push/pull of the outer sheath. See, for example, FIG. 2.

The catheter systems described herein are particularly suitable for needle-through-the-catheter designs. However, the systems may also be used with a catheter-through-the-needle design. Furthermore, a rigid, semi-sharp catheter can altogether replace the need for a needle. Such a design can involve, for example, a rigid, semi-sharp outer and/or inner sheath.

In embodiments, the catheter systems described herein are effective at preventing back-flow of fluid. For example, in the needle-through-the-catheter design, the catheter hole is larger than the needle hole so it creates a plug. Also for example, where the tissue lock is a malecot, the malecot protrudes from the catheter and produces an even greater plug effect. Furthermore, the catheters described herein are designed/configured to minimize fluid flow along the outer wall. For example, extravascular catheters must allow fluid flow along the outer wall. In the case of the catheters described herein, but we are minimizing any fluid flow on the outer surface of the catheter, in either direction (back flow or forward flow).

Materials and Preparation

The catheter systems are prepared from suitable materials such as those described herein. In embodiments, the catheter is prepared from a polymer material, such as nylon, HTPE, polyurethane, polyethylene, PEEK, etc. For example, the inner and outer sheaths are both polymer materials, with the selection of polymer being guided by the desired properties (sterilizable, flexible, non-porous, etc.). The inner and outer sheaths may be made from different materials or may be made from the same material.

Adhesives can be used during assembly of the catheter system where appropriate. For example, an adhesive can be used to adhere the inner and outer sheath distal ends together or to adhere parts of the hub together, or parts of the hub to the inner or outer sheath.

Any suitable sterilization method can be used in the production of the catheter systems. Examples include treatment with/by ethylene oxide, autoclave, UV radiation, sonication, and the like.

Methods of Use

The catheter systems described are suitable for indwelling nerve block applications. In embodiments, the catheter is extravascularly implanted an appropriate distance from the target nerve. For example, an appropriate distance (measuring catheter tip to nerve) is less than or equal to 1, 0.8, or 0.5 mm. Generally, the methods described involve navigating the needle/catheter tip to within a distance, and then deploying the tissue lock. Navigating the needle/catheter tip requires the presence of a needle (either within the catheter or housing the catheter, as described herein). The needle is removed after the tissue lock is engaged (i.e., moved to an extended position). If initial placement of the catheter tip is unsuccessful, the catheter may be removed from the patient, the needle re-inserted into the catheter, and placement of the catheter/needle combination can be attempted again. The needle can be a stimulating or non-stimulating needle.

After implantation, there may be intermittent, temporary movements of the catheter away from the nerve, such as when the patient carries out bulk tissue movement, however the catheter tip will return to a position within the appropriate distance. Without wishing to be bound by theory, the tissue lock remains anchored to the same local tissue. Thus, even with macro movement of the local tissue (e.g., movement of muscle by the patient), the catheter returns to the original location when the tissue returns to the original location.

In an aspect is a method of using the nerve block catheter system as above, the method comprising one or more steps selected from: (1) navigating the nerve block catheter system so that the distal tip of the catheter is within pharmacological proximity to a nerve; (2) engaging the tissue lock; (3) delivering a medicament; (4) removing the needle; (5) repeatedly delivering a medicament, either in bolus or continuously, at physician discretion, to effect continuous pain management treatment; (6) disengaging the tissue lock; and (7) removing the catheter.

For example, the method may involve steps (1) and (2). For example, the method may involve steps (1), (2), and (3). For example, the method may involve steps (1), (2), (3), and (4). For example, the method may involve steps (1), (2), (3), (4), and (5). For example, the method may involve steps (1), (2), (3), (4), (5), (6), and (7).

Step (1) may be carried out with or without the use of nerve stimulation, and also carried out with or without the use of ultrasound guidance. Step (3) may further involve detecting a resultant therapeutic effect after delivering the medicament. Steps (6) and (7) are carried out after completion of pain management treatment. Step (5) may be carried out for as long as the catheter remains implanted.

In embodiments, the delivering of step (3) initiates a nerve block. In some such embodiments, if step (3) is carried out but fails, and the nerve block fails to be initiated, or if the nerve block wears off, the method may further comprise detecting a resultant therapeutic effect.

In embodiments, steps (1)-(4) are collectively part of the initial implantation of the catheter. Step (3) is an optional step and may be omitted from the initial implantation. Step (5) is carried out for as long as the catheter remains implanted, and the repeated delivery may be according to a schedule or may be as needed. Steps (6)-(7) are carried out upon completion of pain management treatment or otherwise completion of use of the catheter.

Placing of the catheter tip is either passive or active. For example, the initial placement of the catheter tip may in embodiments involve visualization with a camera or other imaging technique, and such placement is an active, purpose driven activity. In contrast, the homing of the catheter tip to return to an initial position after any displacement (e.g., due to bulk tissue movement by the patient) is a passive activity that results from the anchoring by the tissue lock.

The catheter systems described herein are suitable for delivery of a variety of fluids. Examples include analgesics and anesthetics. Other fluids such as those suitable for long-term pain management (e.g., alcohol, etc.) are also suitable for delivery.

The catheter systems may be used/implanted for a variety of reasons or medical procedures. The system may be implanted pre-operatively, intra-operatively, or post-operatively as desired. The catheter may also be used post-discharge, e.g., for pain management. Thus, the catheter systems enable de-coupling of implantation from use—the implantation step may be done at the convenience of the using physician and/or patient, and the implanted catheter system may be used as needed.

Some specific suitable applications include: anesthesia related procedures (e.g., continuous epidural anesthesia, continuous spinal anesthesia, continuous peripheral nerve block); pain management procedures (e.g., catheter based intradisc procedures such as nucleoplasty, thermal annular procedures such as IDET and biacuplasty, traditional and functional discography, pulse and water-cooled radiofrequency, spinal cord stimulator, peripheral nerve stimulator, continuous intrathecal drug delivery systems such as intrathecal pump); surgical applications (e.g., surgical drains, nephrostomy drains; Foley catheters); epidurals; and the like.

The catheter devices are intended and suitable for extravascular use only. The catheter devices are not suitable and are not intended for use as intravascular catheters.

The catheter devices are suitable for use by a physician. As used herein, a "using physician" includes, e.g., anesthesiologists and other physicians involved in the medical procedures described herein as suitable for the catheter devices (e.g., pain management, surgery, etc.).

Figure 1:
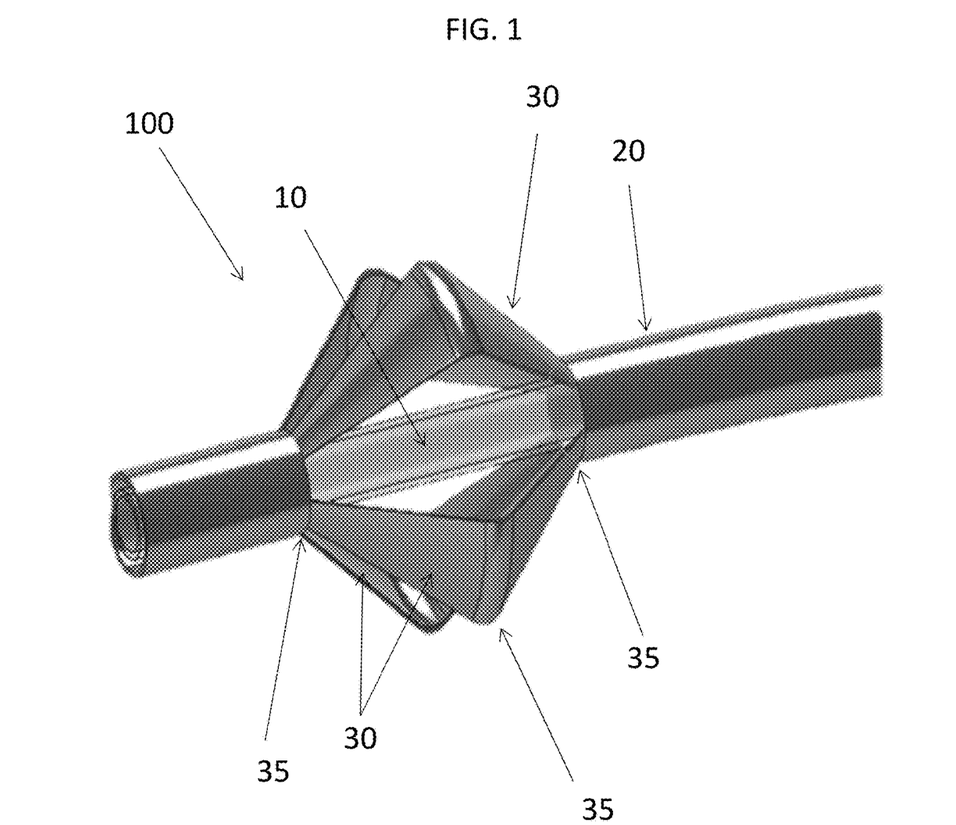
FIG. 1 is a drawing of a catheter according to an embodiment, including a malecot tissue lock.

Referring now to FIG. 1, catheter 100 is shown and comprises outer sheath 20 surrounding inner sheath 10. Outer sheath 20 comprises a plurality of lengthwise slits (not numbered) that define a plurality of malecot extensions 30. Malecot extensions 30 comprise living hinges 35.

Figure 2:
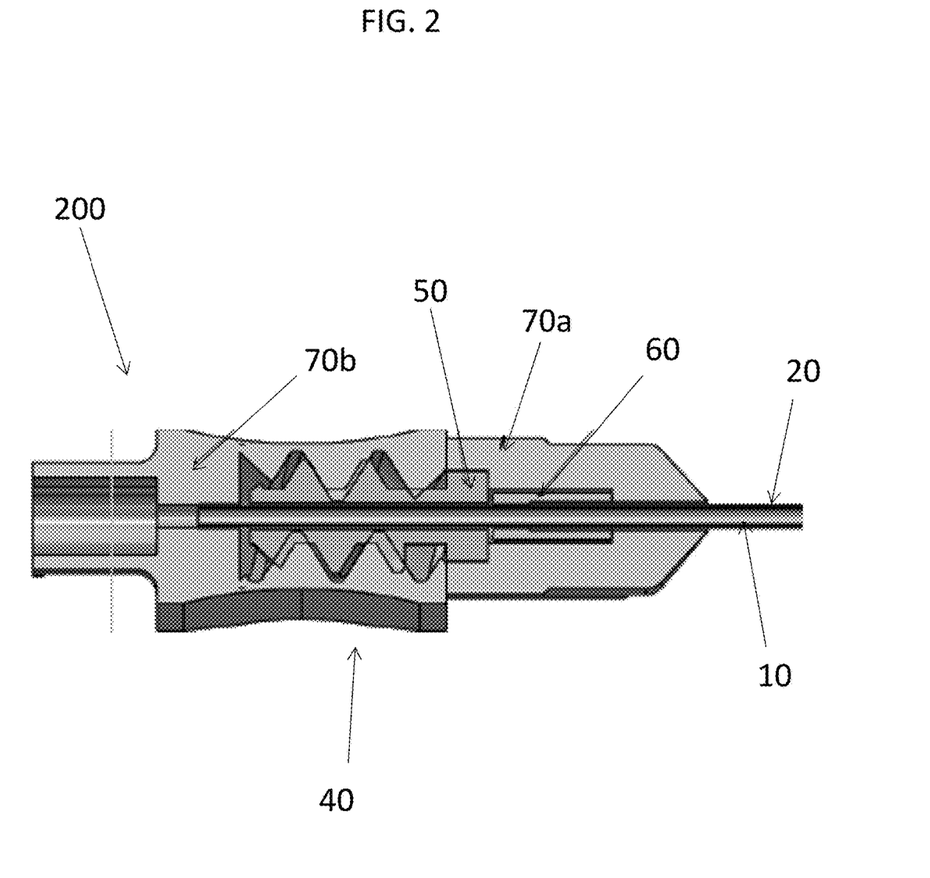
FIG. 2 is a drawing of a catheter system according to an embodiment, including an actuator and catheter.

Referring now to FIG. 2, catheter system 200 is shown and comprises outer sheath 20 surrounding inner sheath 10. Actuator 40 comprises male threads 50 and outer sheath collar 60. Outer sheath collar 60 provides an interface between male threads 50 and outer sheath 20. Actuator 40 is part of a hub comprising round hub 70a and square hub 70b.

Figure 3:
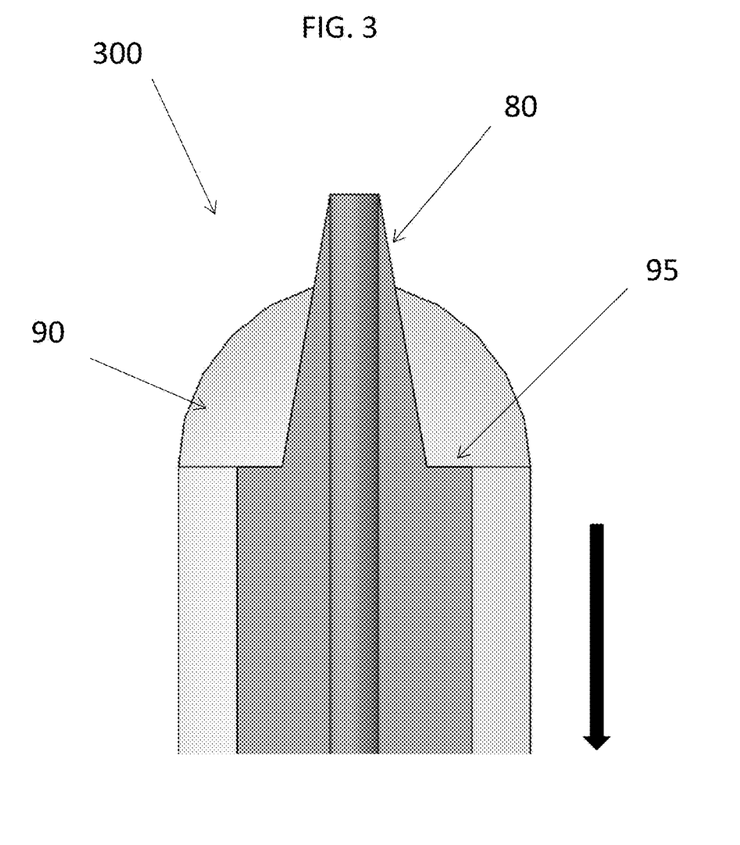
FIG. 3 is a drawing of a catheter distal end according to an embodiment, including a needle through the catheter and a catheter lip.

Referring now to FIG. 3, catheter system 300 is shown and comprises needle 80 disposed within catheter 90. Catheter 90 comprises lip 95, which provides a block against which needle 80 can push. During placement of the catheter, as the catheter is inserted into the patient, the catheter encounters an axial force in the direction of the solid black arrow shown in FIG. 3. Lip 95 prevents the distal section of the catheter from sliding up the needle during insertion, which could cause unintended expansion of the tissue lock (not shown). Thus lip 95 helps to prevent premature deployment of the tissue lock.

In embodiments, the technology described herein reduces/eliminates catheter migration and thereby enables an using physician to confidently place the catheter preoperatively. The implanted catheter is used to administer bolus injections pre-op, intra-op, as well as intermittently post-op for more long term pain management. This improves flow of care. The catheter can be attached to a balloon pump for postop pain management with a constant drip feed of anesthesia, or can be used with a pump that gives intermittent bolus injections. The described methods decrease operating room (OR) time spent on catheter placement, and decrease the use of narcotics for post-op pain management. In embodiments the methods and devices allow single shot bolus delivery and/or continuous anesthesia delivery starting in pre-op, without having to re-do the needle insertion procedure. The catheter system may be used for either bolus or continuous infusion, or a combination thereof. Furthermore, bolus or continuous infusion (either or both) may be used pre-operatively, intra-operatively, or post-operatively.

It is to be understood that while the invention has been described in conjunction with examples of specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. Any combination of the embodiments described herein is intended to be part of the invention, as if all such combinations had been laboriously set forth in this disclosure.

EXAMPLES

Typical usage example: ACL repair. Using previous methods, i.e., a Single Shot Peripheral Nerve Block, patient receives prescription narcotics that cause nausea and vomiting, and that reduce patient satisfaction. Alternatively, an intra-op nerve block (NB) replaces the narcotics. These options, however, do not address using physician needs, require excessive operating room time, and are costly. Furthermore, current methods involving a Continuous Peripheral Nerve Block often require the patient to use a prescription balloon pump that has a high failure rate. In contrast, the catheter system described herein reduces the use of balloon pumps and can improve the flow of care.

A device according to the disclosure and having malecot extensions as tissue lock was prepared, implanted and the tissue lock activated. The force required to remove the catheter from the muscle tissue was significantly higher than anticipated. In both in vitro and in vivo experiments, a tensile tester was used to show that it could require up to 500 grams of force to dislodge and remove the catheter with the anchor deployed. The average was between 200 and 350 grams.

What is claimed is:

1. An anchoring nerve block catheter system comprising:
(A) a dual-sheath catheter comprising an inner sheath and an outer sheath, wherein the catheter and sheaths have proximate and distal ends, wherein the distal ends of the sheaths are connected, the inner sheath defines a fluid delivery lumen, and the outer sheath comprises a tissue lock movable between a collapsed position and an extended position, wherein the tissue lock forms a reversible tissue anchor when in the extended position, and
(B) an actuator connected to the proximate end of the catheter and configured to activate the tissue lock by sliding the outer sheath length-wise relative to the inner sheath,
wherein the tissue lock is a malecot and the outer sheath comprises a plurality of parallel length-wise slits defining a plurality of malecot extensions, and each of the extensions comprises one or more living hinges operable to increase the force exerted by the extensions on surrounding tissue, and the catheter comprises a coil configured to: (a) provide echogenicity, wherein the coil is embedded in the inner sheath; (b) provide a bidirectional antenna configured to deliver electrical energy to a nerve and to transmit internal electricity from nerve electrical activities; or (c) improve anti-kinking of the catheter in locations prone to kinking, wherein the coil has a length and varied wraps per inch length-wise or varied thickness along the length of the coil, and at least one of the following:
(i) the catheter system comprises one or more protrusions at a skin entry point along the outer sheath configured to prevent backflow leakage of anesthetic;
(ii) the catheter system comprises a weak point in the tissue lock promoting collapse of the tissue lock above an axial force or upon accidental removal of the catheter without deactivating the tissue lock;
(iii) the catheter system further comprises a lip or edge on the distal end of the catheter that forms over a lip or edge of a needle inserted through the inner sheath and is operative to avoid deploying the anchor during insertion; or
(iv) the catheter system further comprises a coating on the tissue lock of a tissue ingrowth inhibitor substance sufficient to inhibit tissue ingrowth, wherein the substance is hyalase, glucocorticoids, methotrexate, or an *allium cepa* extract gel.

2. The catheter system of claim 1, wherein the catheter is configured, when deployed in tissue with the tissue anchor activated, to apply a radial force to the tissue and therefore resist axial movement from an axial force of at least 200 g with earth surface gravity.

3. The catheter system of claim 1, wherein the coil is configured to provide echogenicity, wherein the coil is embedded in the inner sheath.

4. The catheter system of claim 1, wherein a wall of the catheter has a durometer or thickness that is varied to improve anti-kinking.

5. The catheter system of claim 1, further comprising (a) a coating on the tissue lock of a tissue ingrowth inhibitor substance sufficient to inhibit tissue ingrowth; (b) an anti-bacterial coating on the tissue lock.

6. The catheter system of claim 1, wherein the inner sheath is configured to reduce or block fluid from leaking through the tissue lock when in the extended position.

7. The catheter system of claim 1, comprising one or more protrusions at a skin entry point along the outer sheath configured to prevent backflow leakage of anesthetic.

8. The catheter system of claim 1, wherein the tissue lock comprises living hinges at each end and in the middle of each malecot extension operative to strengthen the malecot extensions when in the extended position.

9. The catheter system of claim 1, comprising a weak point in the tissue lock promoting collapse of the tissue lock above an axial force or upon accidental removal of the catheter without deactivating the tissue lock.

10. The catheter system of claim 1, wherein the actuator is a squeeze-type bi-stable mechanism configured such that when squeezed after implantation, it deactivates, thus preventing removal of the catheter without deactivation.

11. The catheter system of claim 1, further comprising a lip or edge on the distal end of the catheter that forms over a lip or edge of a needle inserted through the inner sheath and is operative to avoid deploying the anchor during insertion.

12. The catheter system of claim 1, wherein a fiberoptic camera or lens is positioned through the catheter and configured to directly visualize a nerve or bolus post-block to ensure correct placement, or configured to detect the nerve.

13. The catheter system of claim 1, further comprising an echogenic coating on the catheter distal end or tissue lock configured to improve echogenicity of the catheter distal end or tissue lock.

14. The catheter system of claim 1, wherein the coil is configured to provide a bidirectional antenna configured to deliver electrical energy to a nerve and to transmit internal electricity from nerve electrical activities.

15. The catheter system of claim 1, wherein the coil is configured to improve anti-kinking of the catheter in locations prone to kinking, wherein the coil has a length and varied wraps per inch length-wise or varied thickness along the length of the coil.

16. The catheter system of claim 1, wherein the inner sheath comprises one or more exit ports at the tissue lock to allow multiple exit points for fluid.

17. The catheter system of claim 1, further comprising an anti-bacterial coating on the tissue lock that is silver or copper particles or chitosan.

18. The catheter system of claim 1, further comprising a coating on the tissue lock of a tissue ingrowth inhibitor substance sufficient to inhibit tissue ingrowth, wherein the substance is hyalase, glucocorticoids, methotrexate, or an *allium cepa* extract gel.

19. A method of using the nerve block catheter system of claim 1, the method comprising the following steps:
navigating the nerve block catheter system so that the distal tip of the catheter is within pharmacological proximity to a nerve;
engaging the tissue lock; and
delivering a medicament.

20. A method of making a nerve block catheter system of claim 1, comprising assembling the catheter or system from one or more components.

* * * * *